United States Patent [19]

Grattan

[11] Patent Number: 5,597,583
[45] Date of Patent: Jan. 28, 1997

[54] PHARMACEUTICAL COMPOSITION

[75] Inventor: Timothy J. Grattan, Guildford, England

[73] Assignee: SmithKline Beecham p.l.c., Brentford, England

[21] Appl. No.: 318,739

[22] PCT Filed: Apr. 2, 1993

[86] PCT No.: PCT/GB93/00702

§ 371 Date: Oct. 7, 1994

§ 102(e) Date: Oct. 7, 1994

[87] PCT Pub. No.: WO93/20850

PCT Pub. Date: Oct. 28, 1993

[30] Foreign Application Priority Data

Apr. 10, 1992 [GB] United Kingdom ............... 9207990

[51] Int. Cl.⁶ ............................... A61K 9/14; A61K 9/20
[52] U.S. Cl. .................... 424/464; 424/489; 424/400; 514/937; 514/974
[58] Field of Search .................... 424/464, 466, 424/489, 465, 400; 514/937, 974

[56] References Cited

U.S. PATENT DOCUMENTS 5,019,563  5/1991  Hunter et al. ............... 514/58
5,024,997  6/1991  Motola et al. .............. 514/58

FOREIGN PATENT DOCUMENTS 87116738  11/1987  European Pat. Off. .
88300119  1/1988   European Pat. Off. .
89305535  6/1989   European Pat. Off. .
91120559  11/1991  European Pat. Off. .

*Primary Examiner*—James M. Spear
*Attorney, Agent, or Firm*—James M. Kanagy; William T. King; Edward T. Lentz

[57]  ABSTRACT

An ibuprofen-β-cyclodextrin complex for oral consumption in a solution comprising hot water, obtainable by crystallisation from aqueous solution.

6 Claims, No Drawings

PHARMACEUTICAL COMPOSITION

This application is a 371 of PCT/GB93/00702 filed Apr. 2, 1993.

This invention relates to a pharmaceutical composition containing ibuprofen, a process for its preparation, and a palatable formulation thereof suitable for oral consumption. In particular, the invention relates to an ibuprofen-cyclodextrin clathrate complex suitable for formulation in aqueous solution as a hot drink.

Ibuprofen, (±)-2-(p-isobutylphenyl)propionic acid, belongs to the group of non-steroidal antiinflammatory agents (NSAIDs) and is widely indicated for the relief of pain and inflammation in disease states such as arthritis and for treatment of symptoms associated with the common cold and flu. Formulation of the drug into a preparation suitable for oral administration, in particular into a water-soluble form suitable for liquid dosing is complicated by its poor water solubility, its irritating odour and its unpleasant taste. It is an object of the present invention to provide a palatable pharmaceutical composition containing ibuprofen formulated for oral dosing as an aqueous solution.

The ability of drug-cyclodextrin complexes to enhance water solubility and to mask unpleasant taste and odour has been known for many years. In this respect, ibuprofen has proved to be very suitable as a candidate for complexation with cyclodextrins.

Japanese patent publication, JP 56-46837 (Kowa Yakuhin Kogyo) discloses a method for the preparation of an ibuprofen-β-cyclodextrin clathrate complex involving the combination of ibuprofen with β-cyclodextrin in water at elevated temperature and isolation of the clathrate by spray-drying. This method is reported to yield a product containing a high percentage of ibuprofen with a molar ratio of ibuprofen to β-cyclodextrin in excess of 0.7. The increase in water solubility of the drug is considerable, being raised more than 8-fold from 10.44mg per 100 ml to 89.38 mg per 100 ml at 27° C.

The water solubility achieved by complexation with β-cyclodextrin, although significant, is not considered sufficient to permit formulation of ibuprofen as a soluble dosage form for oral administration in liquid form wherein ibuprofen is present at a therapeutic dosage level (100–600 mg) in a suitable volume of water (120–250 ml).

European patent publication 274 444 (Bristol Myers) describes the preparation of ibuprofen-cyclodextrin complexes using α-cyclodextrin, γ-cyclodextrin or a methylated β-cyclodextrin in place of β-cyclodextrin. The water solubility of the ibuprofen-cyclodextrin complex is further enhanced to levels of practical utility using these forms of cyclodextrin, but the high cost of these materials, reflected in the cost of medicinal products containing them, is unlikely to promote their widespread use in analgesic products, more particularly in products available for self medication for the treatment of minor aches and pains and the symptomatic relief of colds and flu.

United Kingdom patent publication GB 2,219,585 (Reckitt & Colman) discloses a complex of β-cyclodextrin with the sodium, potassium, ammonium, magnesium, calcium, arginine, glycine or lysine salt of ibuprofen, having a molar ratio of ibuprofen to β-cyclodextrin in the range 1:0.2 to 1:0.75 and possessing good water solubility. These complexes are not entirely suitable for incorporation into formulations intended for oral consumption in liquid form since, on solution in water, they confer a somewhat unpleasant, soapy taste, typical of an alkaline solution.

The present invention provides an ibuprofen-cydodextrin complex which is suitable for administration as an aqueous solution, which is palatable and yet which is relatively simple and inexpensive to manufacture in comparison with prior art ibuprofen-cyclodextrin complexes.

According to the present invention there is provided the use of an ibuprofen-β-cyclodextrin complex for the manufacture of a medicament for oral consumption as an aqueous solution, characterised in that the complex is administered in a solution comprising hot water.

It has been found that an approximately 30-fold increase in solubility can be achieved by dosing an ibuprofen-β-cyclodextrin complex in aqueous solution at elevated temperatures. It is therefore possible to achieve therapeutic dosage levels of ibuprofen in solution in a single-dose liquid formulation. An ibuprofen-β-cyclodextrin complex for use in the present invention can accommodate a concentration of ibuprofen which will deliver a single dose of up to 600 mg in a volume of 200 ml.

Despite the known increase in solubility of many materials in water with increasing temperature, the practical reality of an ibuprofen liquid hot remedy is surprising. It has been reported that cyclodextrin complex stability constants decrease rapidly with increasing temperature (JACS, 101, 1864, (1979) and JCS Perkin Trans., 2, 15, (1984)). It may therefore be anticipated that dissolution in water as temperature is increased will be accompanied by a concomitant release of ibuprofen from the complex to give an undesirable oily mixture, due to the reduction in the stability constant for the ibuprofen-β-cyclodextrin complex. Contrary to this expectation, it has now been found that ibuprofen-β-cyclodextrin complexes remain homogeneous and stable in water up to a temperature of 100° C.

By utilising the enhanced water solubility of ibuprofen-β-cydodextrin complexes at elevated temperature, there is moreover no necessity for oral administration of solutions at alkaline pH as is necessary for the cyclodextrin complexes described in GB 2, 219,585. According to the present invention, ibuprofen-β-cyclodextrin complexes may be administered as pleasant tasting solutions in the pH range 2.5 to 7.0.

In another aspect of the invention there is provided a process for the preparation of an ibuprofen-β-cyclodextrin clathrate complex. Ibuprofen-β-cyclodextrin clathrate complexes have previously been prepared by several methods including co-precipitation, freeze-drying and neutralisation precipitation methods. Each of these methods requires the use of either alkalis or organic solvents; stringent purification methods are therefore required. The spray-drying process described in JP 56-46837 avoids the use of these reagents; spray-drying is however both costly and time consuming. In contrast to the prior art processes, the process according to the present invention is both convenient and cost effective as a production method and utilises only water in addition to ibuprofen and β-cyclodextrin.

The process according to the invention comprises heating ibuprofen and β-cyclodextrin in water to form a solution, suitably to a temperature of 100° C., followed by crystallisation of the ibuprofen-β-cyclodextrin complex from the solution thus formed, suitably by maintaining the solution in the temperature range −5° to 20° C. Ibuprofen-β-cyclodextrin complexes with an ibuprofen to β-cyclodextrin molar ratio in the range 1:1 to 1:3 are obtainable according to the process of the invention.

An ibuprofen-β-cyclodextrin complex obtainable by the process of crystallisation from aqueous solution forms an aspect of the present invention. Whilst ibuprofen-β-cyclodextrin clathrate complexes prepared by known art methods may be utilised in formulations of the invention, an ibuprofen-β-cyclodextrin complex obtainable by the process of crystallisation from aqueous solution is preferred for use in a liquid formulation for oral administration as hereinbefore described.

A complex of the invention may be formulated in any convenient form, for example as a tablet for solution, or alternatively in powder or granular form for reconstitution with water. Accordingly, the invention provides a pharmaceutical composition comprising an ibuprofen-β-cyclodextrin complex obtainable by crystallisation from aqueous solution in admixture with a pharmaceutically acceptable carrier.

Use of an ibuprofen-β-cydodextrin complex as prepared by the process of the invention is not limited to oral administration in aqueous solution at elevated temperature. Complexes of the invention may be formulated for oral administration in any convenient form, for example as a swallow or chewable tablet, or as a liquid suspension.

A complex obtainable by crystallisation from aqueous solution may be formulated with any appropriate carrier or adjuvant appropriate to the chosen dosage form. Thus, compositions of the invention may include for example preservatives, suspending agents, flavouring agents, bulking agents, binders, adhesives, lubricants, disintegrants, colouring agents, sweetening agents, adsorbents, thickeners and diluents, appropriate to their form.

Compositions of the invention containing an ibuprofen-β-cydodextrin complex may in addition include other pharmaceutical agents suitable for administration therewith, including for example other analgesics, antiinflammatories and antipyretics and also expectorants, antihistamines, decongestants and antitussive agents, such as for example phenypropanolamine, phenylephrine, pseudoephedrine, dextromethorphan, caffeine, codeine and ascorbic acid.

The following Examples are illustrative of the invention. Example 5 which falls outside the scope of the invention is included for comparison.

In the Examples, unless otherwise stated, the abbreviation βCD refers to β-cyclodextrin undecahydrate (β-cyclodextrin. 11H$_2$O).

EXAMPLE 1

Preparation of βCD/Ibuprofen Clathrate (2.2:1)

βCD (146.5 g, 110 mM) was dissolved in water (1000 ml) at 100° C. Ibuprofen (10.3 g, 50 mM) was added and the resulting solution was dried on trays in a convection oven at 60° C. for 16 hours. The resulting white amorphous product was sieved through a 500 μm screen to yield 132 g of powdered βCD/ibuprofen clathrate containing about 7.0% ibuprofen ( 400 mg ibuprofen per 5714 mg of clathrate).

EXAMPLE 2

Preparation of βCD/Ibuprofen Clathrate (1.1:1)

βCD (146.6 g, 110 mM) was dissolved in water (1000 ml) at 100° C. Ibuprofen (20.6 g, 100 mM) was added and the resulting solution was cooled to 1° C. to give a white crystalling precipitate which was washed with cold water and dried at 50° C. for 4 hours in a convection oven. The product, a white solid, was sieved through a 500 μm screen to yield 125 g of βCD/ibuprofen clathrate, containing about 14% ibuprofen ( 400 mg ibuprofen per 2857 mg of clathrate).

EXAMPLE 3

Preparation of a Pharmaceutical Composition containing Ibuprofen/βCD Clathrate for Reconstitution with Hot Water The following ingredients were sieved through a 500 μm screen and mixed together to give a homogeneous white powder:

| | |
|---|---|
| Ibuprofen/βCD Clathrate (Example 1) | 5714 mg |
| Sucrose | 1876 mg |
| Sodium Citrate | 430 mg |
| Citric Acid | 680 mg |
| Saccharin Sodium | 40 mg |
| Lemon Flavour | 60 mg |
| Sodium Cyclamate | 60 mg |

The resulting powder was dissolved in 150 ml of hot water to give a clear, pleasant tasting solution containing 400 mg of ibuprofen per 150 ml of water.

EXAMPLE 4

Preparation of Pharmaceutical Composition containing Ibuprofen/βCD Clathrate for Reconstitution with Hot Water The following ingredients were sieved through a 500 μm screen and mixed together to give a homogeneous white powder:

| | |
|---|---|
| Ibuprofen/βCD Clathrate (Example 2) | 2857 mg |
| Sucrose | 1733 mg |
| Sodium Citrate | 430 mg |
| Citric Acid | 680 mg |
| Saccharin Sodium | 40 mg |
| Lemon Flavour | 200 mg |
| Sodium Cyclamate | 60 mg |

The resulting powder was dissolved in 200 ml of hot water to give a clear, pleasant tasting solution containing 400 mg ibuprofen per 200 ml of water.

EXAMPLE 5

Preparation of a Pharmaceutical Composition containing Ibuprofen for Reconstitution with Hot Water The following ingredients were sieved through a 500 μm screen and mixed together to give a homogeneous white powder:

| | |
|---|---|
| Ibuprofen | 400 mg |
| Sucrose | 3590 mg |
| Sodium Citrate | 430 mg |
| Citric Acid | 680 mg |
| Saccharin Sodium | 40 mg |
| Lemon Flavour | 200 mg |
| Sodium Cyclamate | 60 mg |

The resulting powder was added to 200 ml of hot water to give a turbid suspension. The suspension was considered to be organoleptically unacceptable with a bitter/numbing effect on the oral mucous membrane.

I claim:

1. A method for oral dosing of ibuprofen comprising administering to a patient an ibuprofen-β-cyclodextrin complex in a solution comprising hot water, wherein the ibuprofen β-cyclodextrin complex delivers a therapeutic dosage level of 100 to 600 mg ibuprofen in solution as a single dosage unit, in a pH range of 2.5 to 7.0, and wherein the β-cyclodextrin of the ibuprofen-β-cyclodextrin complex is derived from β-cyclodextrin undecahydrate.

2. The method of claim 1 wherein the solution additionally comprises one or more of the group consisting of a preservative, a suspending agent, a flavouring agent, a bulking agent, a binder, an adhesive, a lubricant, a disintegrant, a colouring agent, a sweetening agent, an adsorbent, a thickener and a diluent.

3. The method of claim 1 wherein the solution additionally comprises one or more of the group consisting of an analgesic, an antiinflammatory, an antipyretic, an expectorant, an antihistamine, a decongestant and an antitussive.

4. A composition for oral consumption comprising an ibuprofen-β-cyclodextrin complex in hot aqueous solution having a pH in the range 2.5 to 7.0, wherein said composition delivers a therapeutic dosage level of 100 to 600 mg ibuprofen in solution as a single dosage unit, and further wherein the β-cyclodextrin of the ibuprofen-β-cyclodextrin complex is derived from β-cyclodextrin undecahydrate.

5. The composition of claim 4 further comprising one or more of the group consisting of a preservative, a suspending agent, a flavouring agent, a bulking agent, a binder, an adhesive, a lubricant, a disintegrant, a colouring agent, a sweetening agent, an adsorbent, a thickener and a diluent.

6. The composition of claim 4 further comprising one or more of the group consisting of an analgesic, an antiinflammatory, an antipyretic, an expectorant, an antihistamine, a decongestant and an antitussive.

\* \* \* \* \*